(12) United States Patent
Freire Martins et al.

(10) Patent No.: US 12,378,283 B2
(45) Date of Patent: Aug. 5, 2025

(54) PROCESS FOR PURIFYING AN ANTIBODY FROM EGG YOLK, PRODUCTS AND USES THEREOF

(71) Applicant: UNIVERSIDADE DE AVEIRO, Aveiro (PT)

(72) Inventors: Mara Guadalupe Freire Martins, Aveiro (PT); Sandra Cristina Da Silva Bernardo, Rio de Mouro (PT); João Manuel Da Costa E Araújo Pereira Coutinho, Ílhavo (PT)

(73) Assignee: UNIVERSIDADE DE AVEIRO, Aveiro (PT)

( * ) Notice: Subject to any disclaimer, the term of this patent is extended or adjusted under 35 U.S.C. 154(b) by 779 days.

(21) Appl. No.: 17/268,854

(22) PCT Filed: Sep. 20, 2019

(86) PCT No.: PCT/IB2019/057993
§ 371 (c)(1),
(2) Date: Feb. 16, 2021

(87) PCT Pub. No.: WO2020/058936
PCT Pub. Date: Mar. 26, 2020

(65) Prior Publication Data
US 2021/0253632 A1 Aug. 19, 2021

(30) Foreign Application Priority Data
Sep. 20, 2018 (PT) .......................... 115028

(51) Int. Cl.
*C07K 1/30* (2006.01)
*C07K 16/02* (2006.01)

(52) U.S. Cl.
CPC .............. *C07K 1/30* (2013.01); *C07K 16/02* (2013.01)

(58) Field of Classification Search
None
See application file for complete search history.

(56) References Cited

U.S. PATENT DOCUMENTS

| 5,367,054 A | 11/1994 | Lee |
| 2006/0223986 A1 | 10/2006 | Chiou |
| 2008/0214795 A1 | 9/2008 | Ramanan et al. |
| 2010/0261886 A1 | 10/2010 | Arunakumari et al. |
| 2011/0015374 A1 | 1/2011 | Mason et al. |
| 2014/0073766 A1 | 3/2014 | Henderson et al. |

FOREIGN PATENT DOCUMENTS

| CN | 103360491 A | 10/2013 | |
| KR | 100471117 B1 * | 12/2001 | ............. C07K 16/02 |
| KR | 20020023521 A | 3/2002 | |
| WO | WO 2014126487 A2 | 8/2014 | |

OTHER PUBLICATIONS

Akita, E.M.; Nakai, S. "Immunoglobulins from Egg Yolk: Isolation and Purification." vol. 57, No. 3, 1992. Journal of Food Science. pp. 629-634. (Year: 1992).*
Amaro, W.A; Al-Qaisi, W.; and Al-Razem, F. "Production and purification of IgY antibodies from chicken egg yolk" vol. 16, 2018. Journal of Genetic Engineering and Biotechnology. pp. 99-103 (Year: 2018).*
Amro, W.A; et al. "Production and purification of IgY antibodies from chicken egg yolk" vol. 16, 2018. Journal of Genetic Engineering and Biotechnology. pp. 99-103. (Year: 1992).*
Devi, C. Maya, et al. "An improved method for isolation of anti-viper venom antibodies from chicken egg yolk." Journal of biochemical and biophysical methods 51.2 (2002): 129-138. (Year: 2002).*
Pauly, Diana et al. "IgY technology: extraction of chicken antibodies from egg yolk by polyethylene glycol (PEG) precipitation." Journal of visualized experiments : JoVE , 51 3084. May 1, 2011, doi: 10.3791/3084 (Year: 2011).*
Akita and Nakai, Comparison of four purification methods for the production of immunoglobulins from eggs laid by hens immunized with an enterotoxogenic E. coli strain, [in:] Journal of Immunological Methods, 160(2), 207-214, 1993.
Bizhanov and Vyshniauskis, A Comparison of Three Methods for Extracting IgY from the Egg Yolk of Hens Immunized with Sendai Virus, [in:] Veterinary Research Communications, 24(2), 103-113, 2000.
Hatta et al, A Novel Isolation Method for Hen Egg Yolk Antibody, "IgY", [in:] Agricultural and Biological Chemistry, 54(10), 2531-2535, 1990.
Hodek et al, Optimized Protocol of Chicken Antibody (IgY) Purification Providing Electrophoretically Homogenous Preparations, [in:] International Journal of Electrochemical Science, 8, 113-124, 2013.
Polson et al, Isolation of viral IgY Antibodies from Yolks of Immunized Hens, [in:] Immunological Communicaions, 9(5), 475-493, 1980.
E M Akita et al, Immunoglobulins from Egg Yolk: Isolation and Purification, [in:] Journal of Food Science, vol. 57, No. 3,Jan. 1, 1992, p. 629-634.
Wala Ahmad Amro et al, Production and purification of IgY antibodies from chicken egg yolk, [in:] Journal of Genetic Engineering and Biotechnology, vol. 16, No. 1, Oct. 10, 2017, p. 99-103.
Tina Deignan et al, Comparative Analysis of Methods of Purification of Egg Yolk Immunoglobulin, [in:] Food and Agricultural Immunology, vol. 12, No. 1, Mar. 1, 2000, p. 77-85.

(Continued)

*Primary Examiner* — Nghi V Nguyen
(74) *Attorney, Agent, or Firm* — Leason Ellis LLP

(57) ABSTRACT

A process for purifying an antibody from egg yolk is provided in which an egg yolk is centrifuged to obtain an aqueous soluble protein fraction, and the aqueous soluble protein fraction is subjected to at least one precipitation step with a precipitating agent. The aqueous soluble protein is then ultrafiltrated to obtain the purified antibody, and the precipitating agent is then removed.

2 Claims, 4 Drawing Sheets

(56) References Cited

OTHER PUBLICATIONS

Bruno De Meulenaer et al, Isolation and Purification of Chicken Egg Yolk Immunoglobulins: A Review, [in:] Food and Agricultural Immunology, vol. 13, No. 4, Dec. 1, 2001, p. 275-288.

Javier Hernaindez-Campos F et al, Purification of Egg Yolk Immunoglobulin (IgY) by Ultrafiltration: Effect of pH, Ionic Strength, and Membrane Properties, Jan. 13, 2010, vol. 58, No. 1, p. 187-193.

D Pauly et al, IgY Technology: Extraction of Chicken Antibodies from Egg Yolk by Polyethylene Glycol (PEG) Precipitation, [in:] Journal of Visualized Experiments, Jan. 2011, vol. 51; Experimental Protocol.

V S de Paula et al, Applied biotechnology for production of immunoglobulin Y specific to hepatitis A virus, [in:] Journal of Virological Methods, Oct. 2010, vol. 171; Materials and methods, point 2.4.

J Wen et al, Preparation and characterization of egg yolk immunoglobulin Y specific to influenza B virus, [in:] Antiviral Research, Nov. 2011, vol. 93; Materials and methods, point.

\* cited by examiner

PROCESS FOR PURIFYING AN ANTIBODY FROM EGG YOLK, PRODUCTS AND USES THEREOF

CROSS-REFERENCE TO RELATED APPLICATIONS

This application is a U.S. National Stage Application under 35 U.S.C. § 371 of International Patent Application No. PCT/IB2019/057993, filed Sep. 20, 2019, which claims priority to Portugal Patent Application No. 115028, filed Sep. 20, 2018, the contents of which are each hereby incorporated by reference in their respective entireties.

Technical Domain

The present disclosure relates to a fast and simple process for the obtention of high purity immunoglobulins (Igs) or antibodies. These polyclonal antibodies are obtained from egg yolk, representing an alternative way for the acquisition thereof and a renewable and profitable source for the production thereof.

The process described in the present disclosure encompasses several steps in which low cost, biocompatible and selective precipitating agents can be used in conjunction with an ultrafiltration step. By performing this process, a high purity, high yield and low cost IgY-enriched precipitate is obtained when compared with antibodies obtained from mammalian serum (immunoglobulin G, IgG) using the methods currently used and described in the industry, namely chromatographic processes. In particular, with the process described herein it is possible to obtain about 100 to 120 mg of antibodies (Igs), with a purity between 90 and 99%, mostly above 98%, per egg yolk.

BACKGROUND ART

Immunoglobulins (Igs) or antibodies are glycoproteins that can be found in plasma or extracellular fluids in vertebrates, being the major humoral response agent of the immune system and constituting about 20% of all existing proteins in human plasma. Antibodies are produced in responses to pathogens such as bacteria and viruses, or proteins and molecules foreign to the organism.

Specifically, immunoglobulin Y (IgY) is a type of bird antibody functionally equivalent to mammalian immunoglobulin G. IgY is produced by birds, and these antibodies concentrate in the egg yolk during its formation.

These antibodies can be used in immunodiagnostics or for clinical purposes, namely in passive immunization of animals and/or humans. Passive immunization represents an alternative method for the treatment of infections caused by pathogens such as viruses or bacteria. As several cases of bacterial resistance to antibiotics have emerged in recent years, finding alternative methods for the treatment of bacterial infections is an extremely important point for today's society. Therapeutic protection using immunoglobulin Y has been successfully reported in several studies, two patents being found on the application of IgY inhibiting the adhesion of *Helicobacter pylori* bacteria to the human stomach mucosa (K.R. Pat. No. 2002/0023521 and C.N. Pat. No. 103360491).

In passive immunization, it is usual to resort to immunoglobulin G (IgG), which is obtained from the serum of mammals (rabbits, goats, mice, sheep, etc.). However, this process is generally unpleasant for animals as it involves repeated blood collection steps which inclusively may lead to animal death.

Another advantage of using IgY over mammalian-derived antibodies (IgG) is that it can obtain a maximum amount of antibodies in a more cost-effective manner, corresponding to more than 100 mg IgY per chicken egg yolk. To obtain the same amount of IgG, approximately 20 mL of mammalian blood is required, which is equivalent to half of the maximum amount that can be collected per month in a small animal (e.g. rabbit).

The fact that birds are phylogenetically distant from humans brings additional advantages related to the reactivity of these antibodies, since IgY, unlike IgG, is not responsible for activating the complement system of our immune response, nor does it recognize rheumatoid factors because they do not recognize the IgY Fc region, which in turn minimizes a non-specific response and cross-reactivity with mammalian intrinsic IgG, thus avoiding false positives in immunodiagnostic tests and undesirable reactions when used in immunotherapy.

IgY purification has been reported in recent decades by several authors. Precipitation methods have been reported involving various precipitating agents such as ethanol, acetone, chloroform, polyethylene glycol, natural gums and also salts (e.g. ammonium sulfate, sodium citrate, sodium chloride, etc.) (Poison, von Wechmar and van Reqenmortel, 1980; Hatta, Kim and Yamamoto, 1990; Akita and Nakai, 1993; Bizhanov and Vyshniauskis, 2000; Hodek et al., 2013).

There are also patents concerning the purification of IgY from egg yolk. U.S. Pat. No. 5,367,054 describes the use of combining a set of methods including: steps of precipitating egg yolk lipids with caprylic acid; ion exchange and gel filtration chromatographs; ultrafiltration processes; and precipitation of IgY using salts, obtaining at the end of the various process combinations an IgY fraction of at least 90% purity. Subsequently, patent document US 2011/0015374A1 reported the purification of IgY by diluting the egg yolk with water and further purifying the antibodies using an ion exchange chromatographic column followed by concentration thereof by a membrane filtration process and consequent drying, at the end of the process obtaining IgY with a purity between 40% and 98%. Patent documents US 2006/223986A1 and 2014/073766A1 refer the use of precipitating agents, such as salts (e.g. ammonium sulfate), but in this case to selectively precipitate a minor antibody type, IgY delta Fc, which only exists in birds from the Anseriformes order. Alternative purification of proteins, including monoclonal antibodies, by precipitation processes has also been subject of attention by various industries, namely Bristol-Myers Squibb Company which owns an invention describing the use of sodium citrate for protein precipitation (US 2010/0261886A1), and Amgen Inc. which has a patent claiming the precipitation of monoclonal antibodies using polyethylene glycol (US 2008/0214795A1).

Known prior art solutions illustrate the technical problem to be solved by the present disclosure.

GENERAL DESCRIPTION

The present disclosure relates to a process for purifying a polyclonal antibody from high purity egg yolk by several steps, in particular by selective precipitation and ultrafiltration steps.

The antibodies referred to herein (immunoglobulin Y) are obtained from a natural, renewable and inexpensive source, namely the egg yolk of a bird. Poultry eggs, and in particular egg yolk, represent an alternative way of obtaining antibodies, which may be used in passive immunization. Precipitating agents used throughout the whole process are also considered biocompatible and inexpensive.

Immunoglobulin Y is a protein, more specifically a glycoprotein, having a total molecular weight of about 180 kDa and consisting of two identical polypeptide chains of 67-70 kDa each and bonded by a disulfide bridge, each of these "heavy" (Hc) chains also being bond via a disulfide bridge to a 25 kDa "light" chain.

The present disclosure relates to a process for purifying an antibody from egg yolk, wherein the process comprises the following steps:
centrifuging the egg yolk in order to obtain an aqueous soluble protein fraction (SPF); subjecting the aqueous soluble protein fraction to at least one precipitation step with a precipitating agent;
ultrafiltration of the aqueous soluble protein fraction subjected to at least one precipitation step in order to obtain the purified antibody, and removing the precipitating agent.

In one embodiment, the said process may comprise a prior step of freezing and thawing of the egg yolk.

In one embodiment, the step of subjecting the aqueous soluble protein fraction (SPF) to at least one precipitation step with a precipitating agent may comprise a first and a second precipitation step with a precipitating agent.

In one embodiment, the precipitating agent may be selected from the following list: polyethylene glycol, sodium chloride, sodium citrate, ammonium sulfate, or mixtures thereof, preferably sodium chloride, more preferably sodium citrate, even more preferably polyethylene glycol wherein the said polyethylene glycol has a molecular weight between 1000-10000 g/mol, preferably 6000-10000 g/mol, even more preferably 6000 g/mol.

In one embodiment and for best results, the polyethylene glycol may have a concentration between 5-40% ($wt_{polymer}/V_{SPF}$), preferably 8-30% ($wt_{polymer}/V_{SPF}$), even more preferably 8.5-15% ($wt_{polymer}/V_{SPF}$).

In one embodiment, the first precipitation step may be carried out with a concentration of 8.5% ($wt_{polymer}/V_{SPF}$) polyethylene glycol.

In one embodiment, the second precipitation step may be carried out with a 12% concentration ($wt_{polymer}/V_{IgY\ resuspended\ after\ first\ precipitation\ step}$) of polyethylene glycol.

In one embodiment, the step of ultrafiltration of the aqueous soluble protein fraction may be carried out with a filter with pores between 70-150 kDa, preferably 100-150 kDa, even more preferably 150 kDa.

In one embodiment, the said process may comprise a prior step of preserving an egg for 1-12 weeks, preferably 2-5 weeks, even more preferably 3 weeks, and this step may be carried out at a temperature between 2-6° C.

In one embodiment, the said process may comprise a step of separating the egg yolk from the egg white, wherein albumin is removed from the surface of the egg yolk sac membrane before the said membrane is punctured so as to get only the egg yolk.

In one embodiment, the process may comprise a prior step of diluting the egg yolk 5-20 times with water, preferably 6-10 times with water, most preferably 7 times with water. In particular, this prior yolk dilution step is carried out at a pH between 4-6, preferably at a pH of 5.

In one embodiment, the step of freezing the egg yolk may be carried out at a temperature between −20-0° C. for 8-24 hours.

In one embodiment, the step of thawing the egg yolk may be carried out at a temperature between 15-25° C. for 2-10 hours.

In one embodiment, the step of centrifuging the thawed egg yolk in order to obtain an aqueous soluble fraction may be carried out between 2000-5000 g, at a temperature between 4-20° C. and for 45-90 minutes, preferably at 4° C. and for GO minutes.

In one embodiment, the antibody is IgY.

In one embodiment, the egg yolk is preferably chicken egg yolk (*Gallus gallus* domesticus).

The present disclosure also relates to an antibody, in particular IgY, wherein said antibody is obtainable by the process described herein.

DESCRIPTION OF THE FIGURES

For an easier understanding of the present disclosure, figures are herein attached, which represent preferred embodiments which however are not intended to limit the object of the present disclosure.

DETAILED DESCRIPTION

The present disclosure describes a process of obtaining and purifying antibodies, namely immunoglobulin Y (IgY), from egg yolk. Antibodies referred to herein are functionally equivalent to immunoglobulin G present in mammals.

Figure 1:
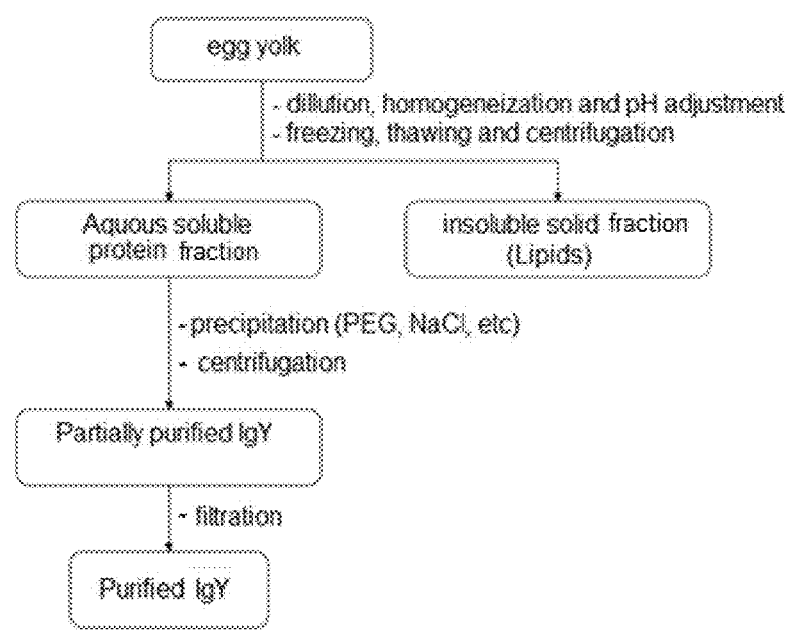
FIG. 1: Schematic diagram of the main steps of the process presented in the present disclosure.
Figure 2:
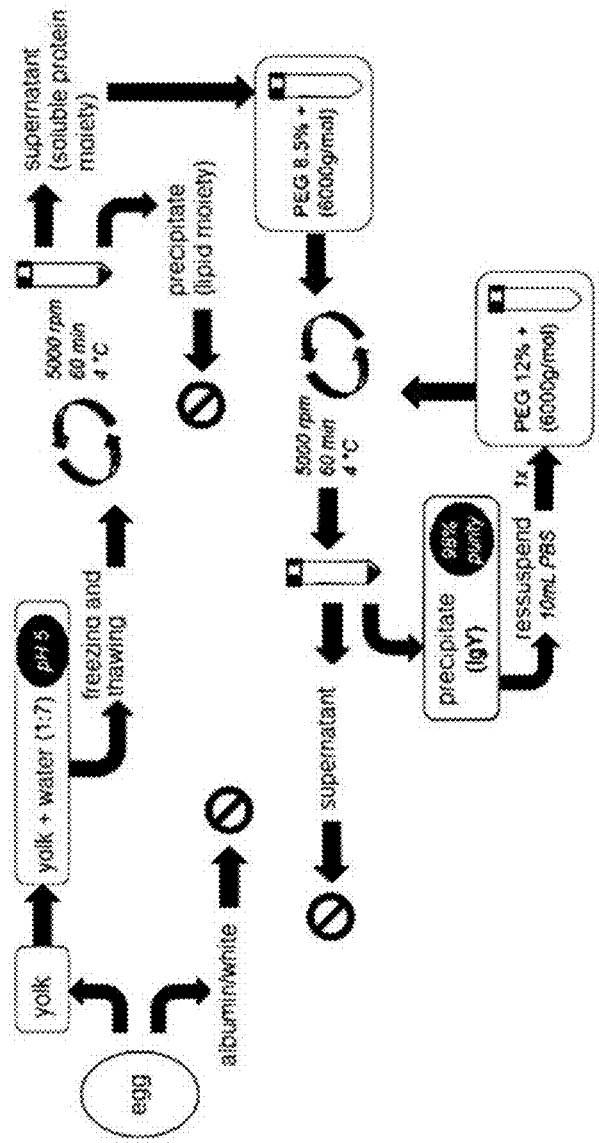
FIG. 2: Detailed schematic diagram of preferred steps and conditions relating to the purification process of the present disclosure.

FIGS. 1 and 2 illustrate preferred embodiments of the process disclosed herein for purifying IgY from chicken egg yolk, wherein said process may comprise several steps, including: separating the egg yolk from the egg white. This step may be carried out so that the entire albumin portion (also called egg white) is removed from the surface of the egg yolk sac membrane before it is punctured to extract the yolk;

diluting the obtained yolk with distilled water, in particular between 6-10 times the initial volume of the yolk and consequently homogenizing the mixture and adjusting its pH, in particular to values between 4-8, preferably pH=5;

the obtained mixture may be subjected to low temperatures (0 to −20° C.) over a period of 8-24 hours and thus the removal of the lipid fraction may be optimized;

the thawing process of the mixture may be carried out at room temperature, in particular at temperatures between 15-25° C. for 2-10 hours;

the thawed mixture may be subjected to a centrifugation process at rotational speeds between 2000-5000 g, at a temperature between 4-20° C. and for 45-90 minutes;

after centrifugation, two fractions are obtained, namely an insoluble solid fraction (lipids) and a clear aqueous fraction, the latter consisting of the yolk soluble proteins;

this soluble protein fraction (SPF) may be filtered in order to remove small suspended solid particles;

the SPF is then subjected to selective precipitation steps with suitable precipitation agents which may include, but not exclusively, polymers such as polyethylene glycol, and/or salts such as sodium citrate, sodium chloride, etc., preferably sodium chloride, most preferably sodium citrate, even more preferably polyethylene glycol;

the final precipitate obtained corresponds to partially purified IgY, in particular with a purity above 90%, which may be resuspended in an appropriate volume of an aqueous buffer solution;

applying a final ultrafiltration step which allows to obtain IgY with a purity between 98-100% while simultaneously allowing the elimination of the precipitating agent(s) used.

Figure 4:
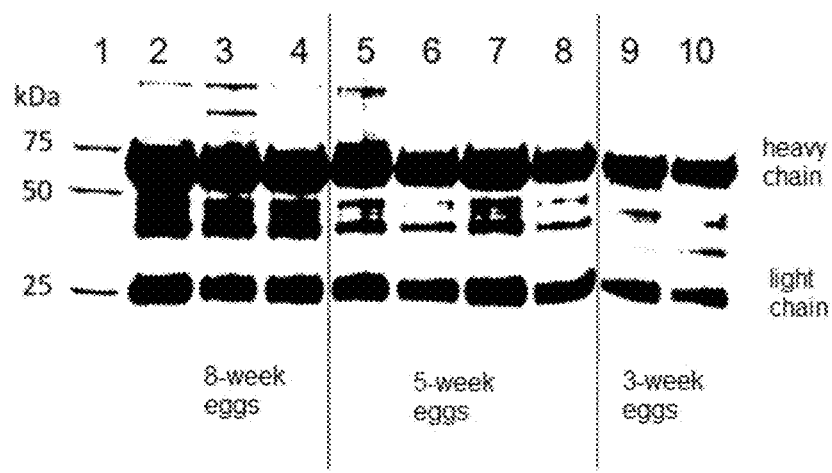
FIG. 4: Reproduction of a Coomassie-blue stained SDS-PAGE gel depicting the results obtained for different egg yolks after carrying out the IgY precipitation process with one of the polymers described in the present disclosure, in particular polyethylene glycol with molecular weight 6000 g/mol. The gel was made under reducing conditions (in the presence of DTT). Position 1 corresponds to the molecular weight standard, "Precision Plus Protein™ Dual Color Standards" (Biorad). Positions 2 to 4 correspond to purified IgY using 8-week egg yolks, positions 5 to 8 correspond to purified IgY using 5-week egg yolks, and positions 9 and 10 correspond to purified IgY using 3-weeks old egg yolks. The amount of protein placed in each of the gel wells was uniformed.
Figure 5:
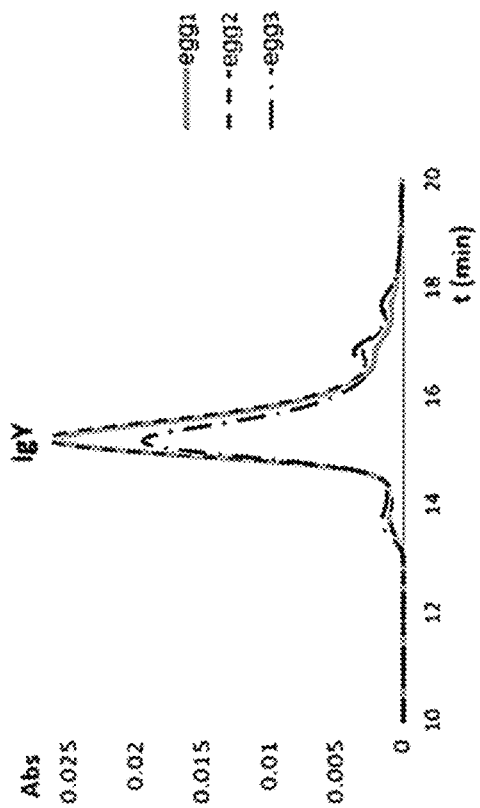
FIG. 5: Evaluation of different egg batches after carrying out the IgY precipitation process with one of the polymers described in the present disclosure, in particular polyethylene glycol with a molecular weight of 6000 g/mo. Chromatograms of different IgY samples and purity assessment, determined by high performance liquid chromatography using a Shodex Protein KW-802.5 molecular exclusion column (SEC-HPLC) (25 cm×2 mm id, 25 μm), and the HPLC Chromaster HPLC (VWR, Hitachi). Eggs 1, 2 and 3, respectively, correspond to 3, 5 and 8 weeks after their collection. Purity was calculated from the peak areas of the chromatograms and using control 1 as standard IgY.

In one embodiment, and in order to obtain a higher amount of IgY at the end of this method, eggs may be preserved after harvesting eggs from immunized chickens for 2-4 weeks after harvesting, preferably 3 weeks (FIG. 4) at a temperature of 2-6° C., the yolks having a total volume of about 15 mL. The advantage of keeping eggs for a few weeks before starting the process is related to a more efficient separation between yolk and albumin.

Figure 3:
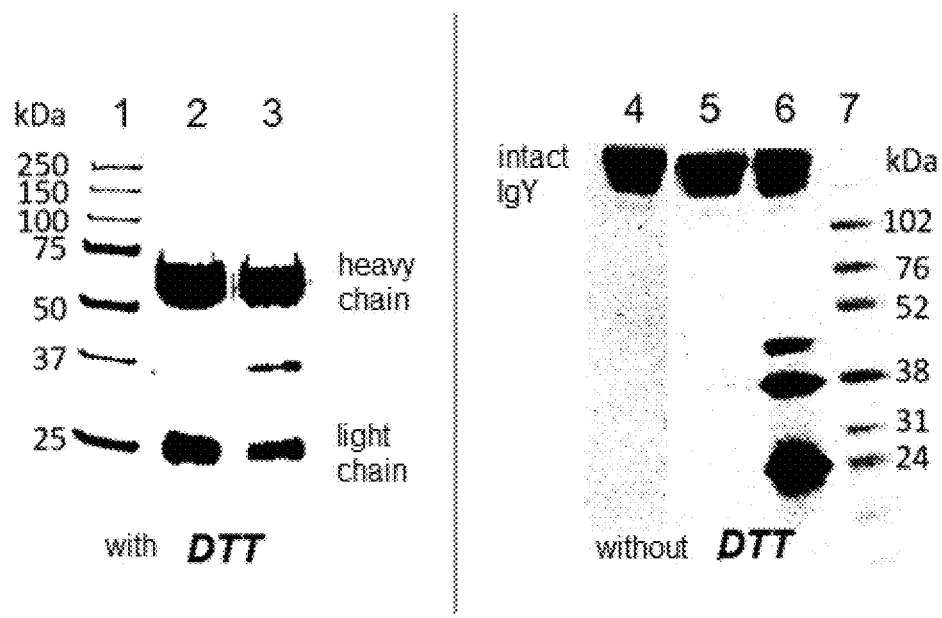
FIG. 3: Reproduction of a gel obtained by sodium dodecyl sulfate polyacrylamide gel electrophoresis (SDS-PAGE) and Coomassie blue stained (Coomassie Brilliant Blue) depicting the results obtained after carrying out the process described in the present disclosure. Positions 1 to 3 correspond to a gel made under reducing conditions (in the presence of dithiothreitol, DTT) and positions 4 to 7 correspond to a gel made under non-reducing conditions (in the absence of DTT). Positions 1 and 7 correspond to molecular weight standards, the first corresponding to "Precision Plus Protein™ Dual Color Standards" (Biorad) and the last to "Full-Range Rainbow Molecular Weight Markers" (Amersham ECL). Positions 2 and 4 correspond to a purified IgY standard (HenBiotech), and positions 3 and 5 correspond to purified IgY using the selective precipitation process with one of the polymers described in the present disclosure, in particular 6000 g/mol molecular weight polyethylene glycol. Position 6 corresponds to the soluble protein fraction. The amount of protein placed in each of the gel wells was uniformed.

Thus, with the process now disclosed it is possible to obtain an IgY precipitate with high purity from the egg yolk, showing the same purity as the same purified antibodies by commonly used chromatographic procedures (FIG. 3). The proposed process does not require the use of expensive chromatographic methods, the precipitating agents used are biocompatible and inexpensive and removed by an ultrafiltration step which further enables the purity of the purified antibody.

Thus, the process described herein allows to purify IgY with a purity above 90%, preferably above 98%, with impurity components being other proteins present in the egg yolk. The overall process yield is between 60% and 90%, preferably above 85%, and it is possible to obtain about 100 to 120 mg of IgY per egg yolk.

The process described in the present disclosure comprises several steps (FIGS. 1 and 2), namely yolk separation and consequent dilution with water and pH adjustment, followed by freezing and thawing of the mixture in order to precipitate the lipid solid fraction, which is removed by a centrifugation step, thereby obtaining the soluble protein fraction (SPF) which is subsequently subjected to selective IgY precipitation steps.

In one embodiment, the precipitate obtained from the process now disclosed is mainly comprised of the desired antibody with a purity higher than 90%, and is resuspended in an aqueous solution of a suitable buffer salt, such as for example an aqueous phosphate-saline buffer solution, in particular 137 mM NaCl, 10 mM potassium phosphate, 2.7 mM KCl, at a pH 7.4.

In one embodiment and for even better results, a final purification and concentration step can be applied by applying an ultrafiltration step, allowing IgY of 98-100% purity to be obtained, while simultaneously removing the precipitating agent.

In one embodiment, the step of separating egg yolk from egg white needs to be carried out with caution so that the entire albumin portion (or egg white) is removed from the surface of the egg yolk sac membrane before it is punctured to obtain the egg yolk exclusively.

In one embodiment, after puncturing the yolk sac membrane, the liquid included therein is poured into a graduated glass container (e.g. graduated beaker) allowing its volume to be recorded. Subsequently, the obtained yolk may be diluted with distilled water to between 6-10 times its initial volume, preferably diluted with 7 times its volume. The advantage of diluting the yolk obtained between 6-10 times is related to the lipid fraction removal efficiency, as diluting less than 6 times has been found to cause a cloudy solution after centrifugation and diluting more than 10 times has resulted in lower yield and purity of IgY in subsequent purification steps.

In one embodiment, the mixture may then be homogenized for about 5 minutes at room temperature, in particular at temperatures between 15-25° C., and its pH may be adjusted with a 1 M HCl solution, to values comprised between 4-8, preferably 5. The reason why the pH is adjusted to 4-8 is due to the lack of stability of IgY outside this range.

In one embodiment, the obtained homogenate may be subjected to a freezing process at temperatures from 0 to −20° C. for a period of 8-24 hours, preferably 12 hours. The thawing process of the mixture may be carried out at room temperature, in particular at a temperature between 15 and 25° C. for 2 to 10 hours, until the mixture is uniformly thawed. The advantages of freezing and thawing the mixture are as follows: the freezing process leads to greater granule aggregation, and thus the lipid fraction can be effectively removed after thawing and subsequent centrifugation.

In one embodiment, the uniformly thawed mixture may then be subjected to a centrifugation process with rotational speeds comprised between 2000-5000 g, at a temperature of 4-20° C. and for 45-90 minutes, more preferably at 4696 g, 4° C. and for 60 minutes. After the centrifugation step, two fractions are obtained: (i) a solid yellowish fraction that is discarded and which constitutes the insoluble (lipid) portion of the egg yolk; and (ii) a clear aqueous fraction consisting of yolk proteins that are water soluble corresponding to the egg yolk soluble protein fraction (SPF). This fraction may be filtered with a filter paper to remove small solid and insoluble particles that are still in suspension.

In one embodiment, the next step of the process described in the present disclosure may comprise selective precipitation of IgY from the above-prepared SPF to give a partially purified IgY precipitate of a purity above 90%, preferably between 95-98% (FIG. 3). Various precipitating agents are used in this step, which may include, but not exclusively, the polyethylene glycol polymer, and/or salts such as ammonium sulfate, sodium citrate, sodium chloride, among others.

In one embodiment, one or two sequential precipitation steps may be implemented, with concentrations of the selected precipitating agent ranging from 5-40% ($wt_{precipitating\ agent}/V_{SPF}$), preferably 30% ($wt_{precipitating\ agent}/V_{SPF}$), even more preferably 8.5% ($wt_{precipitating\ agent}/V_{SPF}$).

In one embodiment, after homogenization of the solution with the selected precipitating agent, the mixture is subjected to a centrifugation process with rotational speeds comprised between 2000-5000 g at a temperature of 4-20° C. and for 45-90 minutes, preferably at 4696 g, at 4° C. and for 60 minutes.

In one embodiment, and if salts are used as precipitating agents, only one precipitation step may be sufficient to obtain a purity above 85%, in which case concentrations above 30% (m/V) of salts as precipitating agents may be selected.

In one embodiment, and preferably, to obtain better purity, above 95%, polyethylene glycol (PEG) may be used as a precipitating agent, wherein the PEG molecular weight may be comprised between 1000-10000 g/mol, preferably 6000-10000 g/mol, preferably 6000 g/mol.

In one embodiment, two sequential PEG precipitation steps can be implemented. PEG concentration in the first step may be comprised between 8-10% (m/V), preferably 8.5% (m/V). After obtaining a first precipitate it is resuspended in a volume of suitable buffer aqueous solution, such as, but not exclusively, 10 mM phosphate buffer pH 7.4 so that a second PEG precipitation is carried out. In this second precipitation step, PEG concentration should be comprised between 10-15% (m/V), preferably 12% (m/V). The final precipitate obtained is partially purified IgY, which has a purity above 90%, preferably a purity between 95-98%. For every 10 mL of SPF used to perform this PEG precipitation step it is possible to obtain about 10 mg of IgY.

In one embodiment, the process may further comprise an ultrafiltration step. The IgY precipitate obtained above is resuspended in an appropriate volume of a buffer solution of choice, in particular 10 mM phosphate buffer and pH 7.4. Then an ultrafiltration step is then implemented with a 70-150 kDa pore filter, preferably 100-150 kDa, even more preferably 150 kDa so that remaining amounts of the precipitating agent used (PEG) and some low molecular weight proteins still present are removed from the solution and thus, a final IgY concentrate with 98-100% purity is obtained.

At the end of this purification process, the amount of IgY obtained and its purity can be determined by conventional analytical methods commonly used for this purpose, including, but not exclusively: sodium dodecyl sulphate polyacrylamide gel electrophoresis (SDS-PAGE) and high performance liquid chromatography with a molecular exclusion column (SEC-HPLC).

Although in the present disclosure only particular embodiments of the invention have been represented and described, the person skilled in the art will know how to introduce modifications and replace technical features for equivalent ones, depending on the requirements of each situation, without departing from the scope of protection defined by the appended claims. The embodiments presented are combinable with each other. The following claims further define embodiments.

REFERENCES

Akita and Nakai (1993) 'Comparison of four purification methods for the production of immunoglobulins from eggs laid by hens immunized with an enterotoxigenic *E. coli* strain', *Journal of Immunological Methods*, 160(2), 207-214.

Bizhanov and Vyshniauskis (2000) 'A Comparison of Three Methods for Extracting IgY from the Egg Yolk of Hens Immunized with Sendai Virus', *Veterinary Research Communications*, 24(2), 103-113.

Hatta et al. (1990) 'A Novel isolation Method for Hen Egg Yolk Antibody, "IgY"', *Agric. Biol. Chem.*, 54(10), 2531-2535.

Hodek et al. (2013) 'Optimized Protocol of Chicken Antibody (IgY) Purification Providing Electrophoretically Homogenous Preparations', *International Journal of Electrochemical Science*, 8, 113-124.

Polson et al. (1980) 'isolation of viral IgY Antibodies from Yolks of Immunized Hens', *Immunological Communications*, 9(5), 475-493.

The invention claimed is:

1. A process for purifying an IgY antibody from egg yolk with a minimum level of purity of 98-%, consisting of:
   diluting the egg yolk 7 times with water, wherein the step of diluting the yolk is carried out at a pH of 5;
   freezing and thawing the egg yolk, wherein the step of freezing the egg yolk is carried out at a temperature between −20-0° C., between 8-24 hours; wherein thawing the egg yolk is carried out at a temperature between 15-25° C., between 2-10 hours;
   centrifuging the egg yolk in order to obtain an aqueous soluble protein fraction (SPF);
   wherein the step of centrifuging the thawed egg yolk in order to obtain the soluble aqueous fraction is carried out at 5000 g, at a temperature of 4° C. and for 60 minutes;
   subjecting the aqueous soluble protein fraction to at least one precipitation step with a precipitating agent;
   ultrafiltrating the aqueous soluble protein fraction subjected to at least one precipitation step in order to obtain the purified antibody, and removing the precipitating agent;
   wherein the step of subjecting the aqueous soluble protein fraction to at least one precipitation step with a precipitating agent comprises a first and a second precipitation step with a precipitating agent, wherein the precipitate obtained on the first precipitation step is resuspended;
   wherein the precipitating agent is polyethylene glycol;
   wherein the polyethylene glycol has a molecular weight between is 6000 g/mol;
   wherein the first precipitation step is carried out with a concentration of 8.5% $wt_{polymer}/V_{SPF}$ polyethylene glycol, and wherein the second precipitation step is carried out with a concentration of 12% $\text{wt}_{polymer}/V_{IgY\ resuspended\ after\ first\ precipitation\ step}$ polyethylene glycol; and wherein the step of ultrafiltration of the aqueous soluble protein fraction is carried out with a filter with pores of 150 kDa, and optionally, a prior step of preserving an egg between 1-12 weeks and/or a step of separating the egg yolk from the egg white, wherein albumin is removed from the surface of the egg yolk sac membrane before said membrane is punctured.

2. The process of claim 1, wherein said step of preserving the egg between 1-12 weeks is carried out at a temperature between 2-6° C.

* * * * *